US009241958B2

(12) United States Patent
Smith et al.

(10) Patent No.: US 9,241,958 B2
(45) Date of Patent: Jan. 26, 2016

(54) ANTICOAGULANT ANTAGONIST AND HEMOPHILIA PROCOAGULANT

(71) Applicant: The Board of Trustees of the University of Illinois, Urbana, IL (US)

(72) Inventors: Stephanie A. Smith, Champaign, IL (US); James H. Morrissey, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/168,195

(22) Filed: Jan. 30, 2014

(65) Prior Publication Data

US 2014/0186462 A1    Jul. 3, 2014

Related U.S. Application Data

(63) Continuation of application No. 12/740,762, filed as application No. PCT/US2008/082225 on Nov. 3, 2008, now abandoned.

(60) Provisional application No. 60/986,924, filed on Nov. 9, 2007.

(51) Int. Cl.
| A61K 33/42 | (2006.01) |
| A61P 7/04 | (2006.01) |
| C12Q 1/56 | (2006.01) |
| G01N 33/86 | (2006.01) |
| A61K 38/36 | (2006.01) |

(52) U.S. Cl.
CPC .......... *A61K 33/42* (2013.01); *A61K 38/36* (2013.01); *C12Q 1/56* (2013.01); *G01N 33/86* (2013.01)

(58) Field of Classification Search
CPC ......... A61K 33/42; A61K 38/36; C12Q 1/56; G01N 33/86; A61P 7/04
See application file for complete search history.

(56) References Cited

U.S. PATENT DOCUMENTS

| 3,983,004 | A | 9/1976 | Trobisch et al. |
| 4,139,619 | A | 2/1979 | Chidsey, III |
| 4,416,812 | A | 11/1983 | Becker et al. |
| 4,684,635 | A | 8/1987 | Orentreich et al. |
| 4,784,944 | A | 11/1988 | Kolde |
| 4,865,984 | A | 9/1989 | Nemerson et al. |
| 4,874,766 | A | 10/1989 | Ooms et al. |
| 5,059,525 | A | 10/1991 | Bartl et al. |
| 5,169,786 | A | 12/1992 | Carroll et al. |
| 5,192,689 | A | 3/1993 | Hemker et al. |
| 5,254,350 | A | 10/1993 | Barrow et al. |
| 5,270,451 | A | 12/1993 | Hawkins et al. |
| 5,298,599 | A | 3/1994 | Rezaie et al. |
| 5,314,695 | A | 5/1994 | Brown |
| 5,338,538 | A | 8/1994 | Tricca et al. |
| 5,358,853 | A | 10/1994 | Butler et al. |
| 5,391,380 | A | 2/1995 | Barrow et al. |
| 5,418,141 | A | 5/1995 | Zweig et al. |
| 5,418,143 | A | 5/1995 | Zweig |
| 5,426,031 | A | 6/1995 | Hawkins et al. |
| 5,472,850 | A | 12/1995 | Morrissey |
| 5,504,067 | A | 4/1996 | Morrissey et al. |
| 5,504,193 | A | 4/1996 | Hawkins et al. |
| 5,508,170 | A | 4/1996 | Butler et al. |
| 5,512,304 | A | 4/1996 | Barrow et al. |
| 5,580,744 | A | 12/1996 | Zweig |
| 5,599,909 | A | 2/1997 | Fickenscher et al. |
| 5,625,036 | A | 4/1997 | Hawkins et al. |
| 5,632,727 | A | 5/1997 | Tipton et al. |
| 5,691,380 | A | 11/1997 | Mason et al. |
| 5,705,477 | A | 1/1998 | Sporn et al. |
| 5,741,658 | A | 4/1998 | Morrissey |
| 5,787,901 | A | 8/1998 | Wilson |
| 5,866,425 | A | 2/1999 | Woodhams et al. |
| 5,888,968 | A | 3/1999 | Chen et al. |
| 5,945,087 | A | 8/1999 | Nelson et al. |
| 5,968,528 | A | 10/1999 | Deckner et al. |
| 6,100,072 | A | 8/2000 | Brucato et al. |
| 6,187,347 | B1 | 2/2001 | Patterson et al. |
| 6,194,394 | B1 | 2/2001 | Hawkins |
| 6,248,353 | B1 | 6/2001 | Singh |
| 6,258,368 | B1 | 7/2001 | Beerse et al. |
| 6,261,803 | B1 | 7/2001 | Zander et al. |
| 6,319,896 | B1 | 11/2001 | Dorin et al. |
| 6,323,326 | B1 | 11/2001 | Dorin et al. |
| 6,355,858 | B1 | 3/2002 | Gibbins |
| 6,376,209 | B2 | 4/2002 | Wissel et al. |
| 6,391,609 | B1 | 5/2002 | Goldford |
| 6,432,657 | B1 | 8/2002 | Kikuchi et al. |

(Continued)

FOREIGN PATENT DOCUMENTS

DE    1617733    4/1971
EP    0 727 434    8/1996

(Continued)

OTHER PUBLICATIONS

Prosecution history for related application U.S. Appl. No. 11/816,401, filed Apr. 2, 2008 (downloaded Apr. 17, 2012), last document dated Apr. 11, 2012, 56 pp.

Prosecution history for related application U.S. Appl. No. 12/680,947, filed Jun. 21, 2010 (downloaded Apr. 17, 2012), last document dated Mar. 8, 2012, 34 pp.

Choi et al. (2010) "Phosphoramidate end labeling of inorganic polyphosphates: Facile manipulation of polyphosphate for investigating and modulating its biological activities," Biochemistry 49:9935-9941.

(Continued)

*Primary Examiner* — Abigail Fisher
(74) *Attorney, Agent, or Firm* — Lathrop & Gage LLP

(57) ABSTRACT

A method for treating a coagulation deficient patient comprises administering an amount of polyP to the patient sufficient to reduce the PT Test value or Dilute PT Test value of the plasma of the patient.

12 Claims, 5 Drawing Sheets

(56) References Cited

U.S. PATENT DOCUMENTS

| | | |
|---|---|---|
| 6,451,610 B1 | 9/2002 | Gorman et al. |
| 6,509,050 B1 | 1/2003 | Henson et al. |
| 6,528,273 B2 | 3/2003 | Hawkins |
| 6,706,861 B2 | 3/2004 | Singh et al. |
| 6,733,985 B1 | 5/2004 | Lee |
| 6,815,424 B2 | 11/2004 | Vickery et al. |
| 7,148,067 B2 | 12/2006 | Morrissey et al. |
| 7,682,808 B2 | 3/2010 | Morrissey et al. |
| 2001/0004641 A1 | 6/2001 | Hawkins |
| 2001/0043951 A1 | 11/2001 | Kim et al. |
| 2002/0012699 A1 | 1/2002 | Singh et al. |
| 2002/0012958 A1 | 1/2002 | Wissel et al. |
| 2002/0019021 A1 | 2/2002 | Kraus |
| 2002/0132370 A1 | 9/2002 | Lassen et al. |
| 2002/0151646 A1 | 10/2002 | Kikukawa et al. |
| 2002/0182225 A1 | 12/2002 | Wang et al. |
| 2003/0064414 A1 | 4/2003 | Benecky et al. |
| 2003/0153084 A1 | 8/2003 | Zheng et al. |
| 2003/0211460 A1 | 11/2003 | Nelsestuen |
| 2004/0037893 A1 | 2/2004 | Hansen et al. |
| 2004/0043933 A1 | 3/2004 | Hansen et al. |
| 2004/0084867 A1 | 5/2004 | Leyland-Jones |
| 2004/0086953 A1 | 5/2004 | Jenny et al. |
| 2005/0282771 A1 | 12/2005 | Johnson |
| 2006/0046309 A1 | 3/2006 | Morrissey et al. |
| 2006/0198837 A1 | 9/2006 | Morrissey et al. |
| 2008/0260858 A1 | 10/2008 | Morrissey et al. |
| 2010/0143492 A1 | 6/2010 | Morrissey et al. |
| 2010/0284998 A1 | 11/2010 | Smith et al. |
| 2010/0297257 A1 | 11/2010 | Smith et al. |

FOREIGN PATENT DOCUMENTS

| | | |
|---|---|---|
| EP | 0 942 284 | 2/1999 |
| WO | WO 93/07492 | 4/1993 |
| WO | WO 98/44352 | 10/1998 |
| WO | WO 99/15196 | 4/1999 |
| WO | WO 00/62742 | 10/2000 |
| WO | WO 00/64471 | 11/2000 |
| WO | WO 00/70084 | 11/2000 |
| WO | WO 2004/094475 | 11/2004 |
| WO | WO 2004/110462 | 12/2004 |
| WO | WO 2005/031303 | 4/2005 |
| WO | WO 2006/031387 | 3/2006 |
| WO | WO 2006/088741 | 8/2006 |
| WO | WO 2006/096345 | 9/2006 |
| WO | WO 2009/046194 | 4/2009 |
| WO | WO 2009/061697 | 5/2009 |

OTHER PUBLICATIONS

Choi et al. (2011) "Polyphosphate is a Cofactor for the Activation of Factor XI by Thrombin," Blood 118:6963-6970.
Müller et al. (2009) "Platelet Polyphosphates Are Proinflammatory and Procoagulant Mediators In Vivo," Cell 139:1143-1156.
Mutch et al. (2010) "Polyphosphate Binds with High Affinity to Exosite II of Thrombin," J Thromb Haemost 8:548-555.
Semeraro et al. (2011) Extracellular Histones Promote Thrombin Generation Through Platelet-Dependent Mechanisms: Involvement of Platelet TLR2 and TLR4, Blood 118:1952-1961.
Smith et al. (2010) "Polyphosphate Exerts Differential Effects on Blood Clotting, Depending on Polymer Size," Blood 116:4353-4359.
Yun et al. (2009) "Polyphosphate and Omptins: Novel Bacterial Procoagulant Agents," J Cell Molec Med 13:4146-4153.
Abstract of : Smith, S.A., et al., "Do elevated plasma tissue factor pathway inhibitor (TFPI) levels affect measurement of factor VIIa?"., Blood, vol. 104, issue 11, (2004).
Abstract of: Smith, S.A. et al., "Polyphosphates—A novel modulator of coagulation"., Arteriosclerosis, Thrombosis, and Vascular Biology, Journal of the American Heart Association, Abstracts of the 6th Annual Conference on arteriosclerosis, Thrombosis and Vascular Biology, vol. 25, 4 pages, (2005).

Aledort, L.M., "Comparative thrombotic event incidence after infusion of recombinant factor VIIa versus factor VIII inhibitor bypass activity", Journal of thrombosis and Haemostasis, 2, pp. 1700-1708 (2004).
Allen, D., "Clotting agents buy wounded troops life-saving time", Stars and Stripes, 3 pages, (2003).
Bader, R., et al. "Multicentric evaluation of a new PT reagent based on recombinant human tissue factor and synthetic phospholipids"., Thrombosis and Haemostasis, vol. 71, No. 3, pp. 292-299, (1994).
Bajzar, L., et al. "TAFI, or plasma procarboxypeptidase B, couples the coagulation and fibrinolytic cascades through the thrombin-thrombornodulin complex"., Journal of Biological Chemistry, vol. 271, No. 28 pp. 16603-16608, (1996).
Bajzar, L., et al. "Thrombin activatable fibrinolysis inhibitor: not just an inhibitor of fibrinolysis"., Crit. Care Med., vol. 32, pp. S320-S324, (2004).
Banner, D.W., et al., "The crystal structure of the complex of blood coagulation factor VIIa with soluble tissue factor"., Nature, vol. 380, pp. 41-46, (1996).
Barrowcliffe, T.W., et al. "Studies of phospholipid reagents used in coagulation I: Some general properties and their sensitivity to factor VIII"., Thrombosis and Haemostasis, Stuttgart, DE, vol. 46, No. 3, pp. 629-633, (1981).
Bladbjerg, E.M., et al., "In vitro effects of heparin and tissue factor pathway inhibitor on factor VII assays. Possible implications for measurements in vivo after heparin therapy"., Blood Coagulation and Fibrinolysis, vol. 11, No. 8, pp. 739-745, (2000).
Boffa, M.B., et al. "Roles of thermal instability and proteolytic cleavage in regulation of activated thrombin-activable fibrinolysis inhibitor"., J. Biol. Chem., vol. 275, pp. 12868-12878 (2000).
Bouma, B.N., et al., Thrombin-activatable fibrinolysis inhibitor (TAFI, plasma procarboxypeptidase B, procarboxypeptidase R, procarboxypeptidase U)., Journal of Thrombosis and Haemostasis, vol. 1, pp. 1566-1574, (2003).
Brody, D.L. et al., "Use of recombinant factor VIIa in patients with warfarin-associated ' ' intracranial hemmorrhage" Neurocritical Care, 2, pp. 263-267, (2005).
Broze, G. J., Jr. "Tissue factor pathway inhibitor"., Thromb. Haemost., vol. 74, pp. 90-93, (1995).
Camerer, E., et al. "Notes on the cell biology of tissue factor"., Haemostasis, vol. 26, pp. 25-30 (1996).
Carr Jr., M.E., et al., "Dextran-Induced Changes in Fibrin Fiber Size and Density Based on Wavelength Dependence of Gel Turbidity", Macromolecules, 13, pp. 1473-1477, (1980).
Carr Jr., M.E., et al., "Effect of Glycosaminoglycans on Thrombin- and Atroxin-Induced Fibrin Assembly and Structure", Thrombosis Haemostasis, 62, pp. 1057-1061, (1989).
Carr Jr., M.E., et al., "Effect of hydroxyethyl starch on the structure of thrombin-and reptilase-induced fibrin gels", J. Lab. Clin. Med. 108, pp. 556-561, (1986).
Carr Jr., M.E., et al., "Influence of $Ca^{2+}$ on the structure of reptilase-derived and thrombin-derived fibrin gels", Biochem. J., 239, pp. 516-516, (1986).
Carr Jr., M.E., et al., "Size and Density of Fibrin Fibers from Turbidity", Macromolecules, 11, pp., 46-50, (1978).
Chikh, G.G., et al., "Attaching histidine-tagged peptides and proteins to lipid-based carriers through use of metal-ion-chelating lipids", Biochim. Biophys. Acta, vol. 1567, pp. 204-212, (2002).
Collen, A., et al., "Unfractionated and Low Molecular Weight Heparin Affect Fibrin Structure and Angiogenesis in Vitro", Cancer Research, 60, pp. 6196-6200, (2000).
Colletier, J-P, et al., "Protein encapsulation in liposomes: efficiency depends on interactions between protein and phospholipid bilayer", BMC Biotechnology, vol. 2, pp. 1-8, (2002).
Cornell, B.A., et al., "Tethered-bilayer lipid membranes as a support for membrane-active peptides"., Biochem. Soc. Trans., vol. 29, pp. 613-617, (2001).
Dano, K., et al., Plasminogen activators, tissue degradation, and cancer., Adv. Cancer Res., vol. 44, pp. 139-266, (1985).
Darst, S.A., "A new twist on protein crystallization"., Proc. Natl. Acad. Sci. USA, vol. 95, pp. 7848-7849, (1998).

(56) References Cited

OTHER PUBLICATIONS

Dickneite, G. et al., "A comparison of fibrin sealants in relation to their in vitro and in vivo properties", Thrombosis Research, vol. 112, pp. 73-82, (2003).
Dickneite, G., et al., "A comparison of fibrin sealants in relation to their in vitro and in vivo properties", Thrombosis Research, 112, pp. 73-82, (2003).
DiStasio, E., et al., "CI Regulates the Structure of the Fibrin Clot", Biophysical Journal, vol. 75, pp. 1973-1979, (1998).
Docampo, R., et al., "Acidocalcisomes—conserved from bacteria to man"., Nature Rev. Microbiol. vol. 3, pp. 251-261, (2005).
Dugan, T.A., et al., "Decorin Modulates Fibrin Assembly and Structure", The Journal of Biological Chemistry, vol. 281, No. 50, pp. 38208-38216, (2006).
Fiore, M.M., et al., "An unusual antibody that blocks tissue factor/factor VIIa function by inhibiting cleavage only of macromolecular substrates"., Blood, vol. 80, pp. 3127-3134, (1992).
Fiore, M.M., et al., "The biochemical basis for the apparent defect of soluble mutant tissue factor in enhancing the proteolytic activities of factor VIIa"., J. Biol. Chem., vol. 269, pp. 143-149, (1994).
Firozvi, K., et al. "Reversal of low-molecular-weight heparin-induced bleeding in patients with pre-existing hypercoagulable states with human recombinant activated factor VII concentrate", American Journal of Hematology, 81, pp. 582-589, (2006).
Gemmell, C.H., et al., "Flow as a regulator of the activation of factor X by tissue factor"., Blood, vol. 72, pp. 1404-1406, (1988).
Gemmell, C.H., et al., "The effects of shear rate on the enzymatic activity of the tissue factor-factor VIIa complex"., Microvasc. Res., vol. 40, pp. 327-340, (1990).
Gemmell., C.H., et al., "Utilization of a continuous flow reactor to study the lipoprotein-associated coagulation inhibitor (LACI) that inhibits tissue factor"., Blood, vol. 76, pp. 2266-2271, (1990).
Gerotziafas, G.T., et al. "Recombinant factor VIIa partially reverses the inhibitory effect of fondaparinux on thrombin generation after tissue factor activation in platelet rich plasma and whole Blood", Thromb. Haemost., 91, pp. 531-537, (2004).
Gibble, et al., "Fibrin glue: the perfect operative sealant?", Transfusion, vol. 30, No. 8, XP002561966, pp. 741-747, (1990).
Groves, J.T., et al., "Supported planar bilayers in studies on immune cell adhesion and communication"., J. Immunol. Methods, vol. 278, pp. 19-32, (2003).
Han, K.Y., et al., "Polyphosphate block tumour metastasis via anti-angiogenic activity", Biochem. J., 406, pp. 49-55, (2007).
Hansen, J-B., et al., "Reduction of factor FVIIa activity during heparin therapy evidence for assay interactions with tissue factor pathway inhibitor and antithrombin"., Thrombosis Research, vol. 100, pp. 389-396, (2000).
Hernandez-Ruiz, L., et al., "Inorganic polyphosphate and specific induction of apoptosis in human plasma cells", The Hematology Journal, 91(9), pp. 1180-1186, (2006).
Hirsh, J.,et al., "American Heart Association/American College of Cardiology Foundation guide to warfarin therapy"., Circulation, vol. 107, pp. 1692-1711, (2003).
Hoots, K., Disseminated Intravascular Coagulation (DIC), Minutes from Jun 18, 2004 meeting, pp. 1-6.
Hoots, W.K., "Challenges in the Therapeutic use of a "So-Called" Universal Hemostatic Agent: Recombinant factor VIIa", American Society of Hematology, Educ. Program, pp. 426-431, (2006).
International Search Report dated Dec. 22, 2006 for PCT application No. PCT/US2006/004789.
International Search Report dated Feb. 10, 2010 for PCT application No. PCT/US2008/078584.
International Search Report dated Feb. 9, 2009 for PCT application No. PCT/2008/082225.
International Search Report Dated Mar. 1, 2006 for PCT application No. PCT/US2005/029873.
International Search Report dated Oct. 5, 2006 for PCT application No. PCT/US2006/006642.

Written Opinion of the International Search Authority dated Aug. 16, 2007 for corresponding for PCT application No. PCT/US2006/004789.
International Preliminary Report of Patentability dated Aug. 21, 2007 for corresponding for PCT application No. PCT/US2006/004789.
Written Opinion of the International Search Authority dated Apr. 5, 2010, for PCT application No. PCT/US2008/078584.
International Preliminary Report of Patentability dated Apr. 7, 2010, for PCT application No. PCT/US2008/078584.
Written Opinion of the International Search Authority dated Jun. 29, 2009 for PCT application No. PCT/2008/082225.
International Preliminary Report on Patentability dated Jun. 30, 2009 for PCT application No. PCT/2008/082225.
Written Opinion of the International Search Authority dated Feb. 28, 2007 for PCT application No. PCT/US2005/029873.
International Preliminary Report on Patentability dated Feb. 28, 2007 for PCT application No. PCT/US2005/029873.
Written Opinion of the International Search Authority dated Sep. 4, 2007 for PCT application No. PCT/US2006/006642.
International Preliminary Report of Patentability dated Sep. 12, 2007 for PCT application No. PCT/US2006/006642.
Invitation to Pay Additional Fees and International Search Report for PCT application No. PCT/US2006/004789 dated Oct. 24, 2006.
Jackson, C.M., "Monitoring oral anticoagulant therapy-INR values for the Owren prothrombin time"., Thromb Haemost, vol. 91, pp. 210-212, (2004).
Jackson, M.R., "Fibrin sealants in surgical pracrtive: An overview", The American Journal of Surgery, 182, pp. 1S-7S, (2001).
Jeong, S.W., et al., "Synthesis of a polymerizable metal-ion-chelating lipid for fluid bilayers"., J. Org. Chem., vol. 66, No. 14, pp. 4799-4802, (2001).
Jones, D.T., "Do transmembrane protein superfolds exist?", FEBS Letters, vol. 423, pp. 281-285, (1998).
Kawazoe, Y., et al., "Induction of Calcification in MC3T3-E1 Cells by Inorganic Polyphosphate", J. Dent. Res., 83(8), pp. 613-618, (2004).
Kemball-Cook, G., et al., "High-level production of human blood coagulation factors VII and XI using a new mammalian expression vector"., Gene, vol. 139, pp. 275-279, (1994).
Kent, M.S., et al., "Segment concentration profile of myoglobin adsorbed to metal ion chelating lipid monolayers at the air-water interface by neutron reflection"., Langmuir, vol. 18, No. 9. pp. 3754-3757, (2002).
Kessler et al. (2004), Current and Future Challenges of Antithrombotic Agents and Anticoagulants: Strategies for Reversal of Hemorrhagic Complications, Seminars in Hematology, vol. 41, No. 1, Suppl. 1: pp. 44-50.
Kessler, C.M., "Current and future challenges of antithrombotic agents and anticoagulants: Strategies for reversal of hemorrhagic complications", Seminars in Hematology, 41, pp. 44-50, (2004).
Kitchen, S., et al. "Standardization of prothrombin time for laboratory control of oral anticoagulant therapy"., Seminars in Thrombosis and Hemostasis, vol. 25, No. 1, pp. 17-25, (1999).
Kitchen, S., et al. "Two recombinant tissue factor reagents compared to conventional thromboplastins for determination of international normalised ratio: a thirty-three-laboratory collaborative study"., The Steering Committee of the UK National External Quality Assessment Scheme for Blood Coagulation., Thrombosis and Haemostasis, vol. 76, No. 3, pp. 372-376, (1996).
Korberg, A., et al., "Inorganic Polyphosphate: A Molecule of Many Functions", Annu. Rev. Biochem., 68, pp. 89-125, (1999).
Kornberg, A., "Inorganic polyphosphate: Toward making a forgotten polymer unforgettable"., Journal of Bacteriology. vol. 177, No. 3, pp. 491-496, (1995).
Kornberg, A., et al. "Inorganic polyphosphate: a molecule of many functions", Annu. Rev. Biochem., 68, pp. 89-125, (1999).
Krishnamurthy, G.T., et al. Clinical comparison of the kinetics of $^{99m}$Tc-labeled polyphosphate and diphosphonate, Journal of Nuclear Medicine, 15(10), pp. 848-855, (1974).
Kubalek, E.W., et al., "Two-dimensional crystallization of histidine-tagged, HIV-1 reverse transcriptase promoted by a novel nickel-chelating lipid"., J. Structural Biology, vol. 113, pp. 117-123, (1994).

(56) References Cited

OTHER PUBLICATIONS

Kubitza, D., et al., "Safety, pharmacodynamics, and pharmacokinetics of BAY 59-7939—an oral, direct Factor Xa inhibitor-after multiple dosing in healthy male subjects", Eur J. Clin Pharmacol, 61, pp. 873-880, (2005).

Kulaev, I.S., et al., "Metabolism and Function of Polyphosphates in Bacteria and Yeast", Progress Molecular and Subcellular Biology. vol. 23, pp. 27-43, (1999).

Kumble, K.D., et al., "Inorganic Polyphosphate in Mammalian Cells and Tissues", The Journal of Biological Chemistry, vol. 270, No. 11, pp. 5818-5822, (1995).

Laurer, S.A., et al. "Development and characterization of Ni-NTA-bearing microspheres"., Cytometry. vol. 48, pp. 136-145, (2002).

Lauricella, A.M., et al., "Influence of homocysteine on fibrin network lysis", Blood Coagulation and Fibrinolysis, 17, pp. 181-186, (2006).

Lazarus, R.A., et al. "Inhibitors of Tissue Factor* Factor VIIa for anticoagulant therapy"., Curr. Med. Chem., vol. 11, pp. 2275-2290, (2004).

Lin, J., et al. "The use of recombinant activated factor VII to reverse warfarin-induced anticoagulation in patients with hemorrhages in the central nervous system: preliminary findings", . Neurosurg., 98, pp. 737-740, (2003).

Linkins, L.A., et al., "New anticoagulant therapy"., Annu. Rev. Med., vol. 56, pp. 63-77, (2005).

Lisman T., et al., "Recombinant factor VIIa reverses the in vitro and ex vivo anticoagulant and profibrinolytic effects of fondaparinux", Journal of Thrombosis and Haemostasis, 1, pp. 2368-2373, (2003).

Lorenz, B., et al., "Anti HIV-1 activity of inorganic polyphosphates"., J. Acquir. Immune. Defic. Syndr. Hum Retrovirol., vol. 14, pp. 110-118, (1997).

Lorenz, B., et al., "Mammalian intestinal alkaline phosphatase acts as highly active exopolyphosphatase"., Biochim. Biophys. Acta, vol. 1547, pp. 254-261, (2001).

Luddington R.J. "Thrombelastography/thromboelastometry", Clin. Lab. Haem., vol. 27, pp. 81-90, (2005).

Mann et al. (2003), "Factor V: a combination of Dr Jekyll and Mr Hyde," Blood, 101(1): 20-30.

Marx, P.F., et al., Plasmin-mediated activation and inactivation of thrombin-activatable fibrinolysis inhibitor., Biochemistry, vol. 41, pp. 6688-6696, (2002).

Marx, P.F., et al., "Inactivation of active thrombin-activable fibrinolysis inhibitor takes place by a process that involves conformational instability rather than proteolytic cleavage"., J. Biol. Chem., vol. 275, pp. 12410-12415, (2000).

Massignon, D., et al., "Prothrombin time sensitivity and specificity to mild clotting factor deficiencies of the extrinsic pathway: evaluation of eight commercial thromboplastins"., Thrombosis and Haemostasis, vol. 75, No. 4, pp. 590-594, (1996).

Mathew, P., "Current Opinion on Inhibitor Treatment Options", Seminars in Hematology, 43, pp. S8-13, (2006).

Morrisey, J.H., et al., "Quantitation of activated factor VII levels in plasma using a tissue factor mutant selectively deficient in promoting factor VII activation", Blood, vol. 81, pp. 734-744, (1993).

Morrison, M., et al. "Discrepant INR values: a comparison between Manchester and Thrombotest reagents using capillary and venous samples"., Clin. Lab. Haemat., vol. 11, No. 4, pp. 393-398, (1989).

Morrissey, J.H., "Tissue factor and factor VII initiation of coagulation". In: Colman RW, Hirsh J, Marder VJ, Clowes AW, George JN, editors, Hemostasis and Thrombosis: Basic Principles and Clinical Practice, Philadelphia, Lippincott Williams & Wilkins, pp. 89-101, (2001).

Morrissey, J.H., "Tissue factor: an enzyme cofactor and a true receptor"., Thromb. Haemost., vol. 86, pp. 66-74, (2001).

Morrissey, J.H., et al., "Factor VIIa-tissue factor: functional importance of protein-membrane interactions"., Thromb. Haemost., vol. 78, pp. 112-116, (1997).

Morrissey, J.H., et al., "Molecular cloning of the cDNA for tissue factor, the cellular receptor for the initiation of the coagulation protease cascade"., Cell, vol. 50, pp. 129-135, (1987).

Morrissey, J.H., et al., "Monoclonal antibody analysis of purified and cell-associated tissue factor"., Thromb. Research, vol. 52, pp. 247-261, (1988).

Mosesson, M.W., "Fibrinogen and fibrin structure and functions", Journal of thrombosis and Haemostasis, 3, pp. 1894-1904, (2005).

Mosnier, L.O., et al., "Identification of thrombin activatable fibrinolysis inhibitor (TAFI) in human platelets"., Blood, vol. 101, pp. 4844-4846, (2003).

Mutch, N.J. et al., "Polyphospates—a novel modulator of Fibrinolysis", Journal of Thrombosis and Haemostasis, vol. 93, No. 4, pp. A21, (2005).

Nair, C.H., et al., "Effect of Temperature, pH and Ionic Strength and Composition on Fibrin Network Structure and Its Development", Thrombosis Research, 42, pp. 809-816, (1986).

Nakagaki, T., et al., "Initiation of the extrinsic pathway of blood coagulation: evidence for the tissue factor dependent autoactivation of human coagulation factor VII"., Biochemistry, vol. 30, pp. 10819-10824, (1991).

Nemerson, Y., et al., "Tissue factor accelerates the activation of coagulation factor VII: The role of a bifunctional coagulation cofactor"., Thromb. Res., vol. 40, pp. 351-358, (1985).

Nesheim, M., "Thrombin and fibrinolysis"., Chest, vol. 124, No. 3, pp. 33S-39S, (2003).

Nesheim, M., et al., "Thrombin, thrombomodulin and TAFI in the molecular link between coagulation and fibrinolysis"., Thromb. Haemost, vol. 78, pp. 386-391, (1997).

Neuenschwander, P.F., et al. "Deletion of the membrane anchoring region of tissue factor abolishes autoactivation of factor VII but not cofactor function. Anaysis of a mutant with a selective deficiency in activity"., J. Biol. Chem., vol. 267, pp. 1477-14482, (1992).

Neuenschwander, P.F., et al., "Factor VII autoactivation proceeds via interaction of distinct protease-cofactor and zymogen-cofactor complexes. Implications of a two-dimensional enzyme kinetic mechanism"., J. Biol. Chem., vol. 268, pp. 21489-21492, (1993).

Neuenschwander, P.F., et al., "Phosphatidylethanolamine augments factor VIIa-Tissue factor activity: Enhancement of sensitivity to phosphatidylserine"., Biochemistry, vol. 34, No. 43, pp. 13988-13993, (1995).

Neuenschwander, P.F., et al., Roles of the membrane-interactive regions of actor VIIa and tissue factor. The factor VIIa GIa domain is dispensable for binding to tissue factor but important for activation of factor X., J. Biol. Chem., vol. 269, pp. 8007-8013, (1994).

Nilsson, J., et al., "Comparative analysis of amino acid distributions in integral membrane proteins from 107 genomes"., Proteins, vol. 60, pp. 606-616, (2005).

Noegel, A. et al., "Isolation of a high molecular weight polyphosphate from Neisseria gonorrhoeae", J. Exp. Med., vol. 157, pp. 2049-2060, (1983).

Novotny, W.F., et al., "Platelets secrete a coagulation inhibitor functionally and antigenically similar to the lipoprotein associated coagulation inhibitor"., Blood, vol. 72, pp. 2020-2025, (1988).

O'Connell, K.A., et al., "Thromoboembolic adverse events after use of recombinant human coagulation factor VIIa", JAMA, vol. 295, No. 3, pp. 293-298, (2006).

Oh J.J., et al., "Recombinant factor VIIa for refractory bleeding after cardiac surgery secondary to anticoagulation with the direct thrombin inhibitor lepirudin", Pharmacotherapy, 26, No. 4, pp. 576-577, (2006).

Paborsky, L.R., et al., "Lipid association, but not the transmembrane domain, is required for tissue factor activity. Substitution of the transmembrane domain with a phosphatidylinositol anchor"., J. Biol. Chem., vol. 266, pp. 21911-21916, (1991).

Parise, P., et al., "Effects of low molecular weight heparins on fibrin polymerization and clot sensitivity to t-PA-inducted lysis", Blood Coagulation and Fibrinolysis, vol. 4, pp. 721-727, (1993).

Poller, L., "Activated partial thromboplastin time (APTT)", Laboratory Techniques in Thrombosis: A Manual ($2^{nd}$ revised edition of ECAT Assay Procedures) Kluwer Academic Publishers, Dordrecht, (1999).

Poller, L., et al., "International Normalized Ratios (INR): the first 20 years"., Journal of Thrombosis and Haemostasis, vol. 2, pp. 859-860, (2004).

(56) References Cited

OTHER PUBLICATIONS

Poller, L., et al., "Minimum lyophilized plasma requirement for ISI calibration"., European Concerted Action on Anticoagulation, Am. J. Clin. Pathol., vol. 109, pp. 196-204, (1998).
Radler, U. et al., "Design of supported membranes tethered via metal-affinity ligand-receptor pairs", Biophysical Journal, vol. 79, pp. 3144-3152, (2000).
Repke, D., et al. "Hemophilia as a defect of the tissue factor pathway of blood coagulation: effect of factors VIII and IX on factor X activation in a continuous-flow reactor"., Proc. Natl. Acad. Sci. USA, vol. 87, pp. 7623-7627, (1990).
Rezaie, A.R., et al., "Expression and purification of a soluble tissue factor fusion protein with an epitope for an unusual calcium-dependent antibody"., Protein Expression and Purification, vol. 3, pp. 453-460, (1992).
Rojkjaer, R., et al., "Activation of the plasma kallikrein/kinin system on endothelial cell membranes"., Immunopharmacology, vol. 43, pp. 109-114, (1999).
Roussi, J., et al., "French multicentric evaluation of recombinant tissue factor (recombiplastin) for determination of prothrombin time"., Thrombosis and Haemostasis, vol. 72, No. 5, pp. 698-704, (1994).
Ruf, W., et al., "Phospholipid-independent and dependent interactions required for tissue factor receptor and cofactor function"., J. Biol. Chem., vol. 266, pp. 2158-2166, (1991).
Ruiz, F.A., et al., "Human platelet dense granules contain polyphosphate and are similar to acidocalcisomes of bacteria and unicellular eukaryotes"., Journal of Biological Chemistry, vol. 279, No. 43, pp. 44250-44257, (2004).
Sandset, P.M., et al., "Heparin induces release of extrinsic coagulation pathway inhibitor (EPI)"., Thromb. Res., vol. 50, pp. 803-813, (1988).
Schneider, M., et al., "Two naturally occurring variants of TAFI (Thr-325 and Ile-325) differ substantially with respect to thermal stability and antifibrinolytic activity of the enzyme"., J. Biol. Chem., vol. 277, pp. 1021-1030, (2002).
Schulman, S., et al. "Anticoagulants and Their Reversal", Transfusion Medicine Reviews, Vo. 21, No. 1, pp. 37-48, (2007).
Search from USPTO website dated May 26, 2004, for key words "Factor VII" and thromboplastin.
Search from USPTO website dated May 27, 2004, for key words "Factor VII" and thromboplastin, PGPUB Production Database.
Seddon, A.M., et al., "Membrane proteins, lipids and detergents: not just a soap opera"., Biochim. Biophys. Acta., vol. 1666, pp. 105-117, (2004).
Shigematsu, Y., et al., "Expression of human soluble tissue factor in yeast and enzymatic properties of its complex with factor VIIa"., J. Biol. Chem., vol. 267, pp. 267, pp. 21329-21337, (1992).
Shrout, A.L. et al., "Template-directed assembly of receptor signaling complexes", Biochemistry, vol. 42, No. 46, pp. 13379-13385, (2003).
Smith S.A., et al., "Sensitive Fluorescence detection of polyphosphate in polyacrylamide gels using 4', 6-diamidino-2-phenylindol", Electrophoresis, vol. 28, No. 19, pp. 3461-3465, (2007).
Smith, A., et al., "Properties of recombinant human thromboplastin that determine sensitivity to vitamin K-dependent coagulation factors", Blood, vol. 104, No. 11, part 1, pp. 155A, 46$^{th}$ Annual meeting of the American Society of Hematology, San Diego, CA, USA, Dec. 4-7, 2004.
Smith, S.A. et al., "Polyphosphate enhances fibrin clot structure", Blood, vol. 112, No. 7, pp. 2810-2816, (2008).
Smith, S.A. et al., "Properties of recombinant human thromboplastin that determine the International Sensitivity Index (ISI)"., J. Thromb, Haemost, vol. 2, pp. 1610-1616, (2004).
Smith, S.A., et al. "The various procoagulant effects of PolyP require different minimal polymer lengths", Blood (ASH Annual Meeting Abstracts), 110: Abstract 1761, (2007).
Smith, S.A., et al., "Polyphosphate as a general procoagulant agent", Journal of Thrombosis and Haemostasis, vol. 6, No. 10, pp. 1750-1756, (2008).
Smith, S.A., et al., "Polyphosphate enhances fibrin clot structure", Blood (ASH Annual Meeting Abstracts), 110: Abstract 403, (2007).
Smith, S.A., et al., "Polyphosphate modulates blood coagulation and fibrinolysis"., PNAS, vol. 103, No. 4, pp. 903-908, (2006).
Smith, S.A., et al., "Polyphosphate shortens the clotting time of hemophilic and anticoagulated plasma", Blood (ASH Annual Meeting Abstracts), 110: Abstract 1760, (2007).
Smith, S.A., et al., "Rapid and efficient incorporation of tissue factor into liposomes "., Journal of Thrombosis and Haemostasis, vol. 2, pp. 1155-1162, (2004).
Stone, M.J., et al. "Recombinant soluble human tissue factor secreted by *Saccharomyces cerevisiae* and refolded from *Escherichia coli* inclusion bodies: glycosylation of mutants, activity and physical characterization"., J. Biochem., vol. 310, pp. 605-614, (1995).
Terpe, K. "Overview of tag protein fusions: from molecule and biochemical fundamentals to commercial systems"., Appl. Microbiol. Biotechnol., vol. 60, pp. 523-533, (2003).
Testa, S., et al., "Discrepant sensitivity of thromboplastin reagents to clotting factor levels explored by the prothrombin time in patients on stable oral anticoagulant treatment: impact on the international normalized ratio system"., Haematologica, vol. 87, No. 12, pp. 1265-1273, (2002).
Tripodi, A., et al., "Recombinant tissue factor as substitute for conventional thromboplastin in the prothrombin time test"., Thromb. Haemost, vol. 67, pp. 42-45, (1992).
Van Den Besselaar, A.M.H.P., et al., "Annex 3: Guidelines for thromboplastins and plasma used to control oral anticoagulant therapy"., World Health Organization, Technical Report Series, No. 889, pp. 64-93, (1999).
Wallin, E., et al., "Genome-wide analysis of integral membrane proteins from eubacterial, archaean, and eukaryotic organisms"., Protein Sci., vol. 7, pp. 1029-1038 (1998).
Wang, L., et al., "Inorganic polyphosphate stimulates mammalian TOR, a kinase involved in the proliferation of mammary cancer cells", Proc. Natl. Acad. Sci. U.S.A., vol. 100, No. 20, pp. 11249-11254, (2003).
Waters, E.K., et al. "Restoring full biological activity to the isolated ectodomain of an integral membrane protein"., Biochemistry, vol. 45, No. 11, pp. 3769-3774, (2006).
Watson, C., et al., "Recombinant and tissue extract thromboplastins for determination of international normalized ratio in over-anticoagulated patients"., British Journal of Biomedical Science, vol. 56, pp. 123-127, (1999).
Waxman, E., et al., "Human factor VIIa and its complex with soluble tissue factor: Evaluation of asymmetry and conformational dynamics of ultracentrifugation and fluorescence anisotropy decay methods"., Biochemistry, vol. 32, pp. 3005-3012, (1993).
Waxman, E., et al., "Tissue factor and its extracellular soluble domain: The relationship between intermolecular association with factor VIIa and enzymatic activity of the complex"., Biochemistry, vol. 31, pp. 3998-4003, (1992).
Wolberg A.S., et al., "Elevated prothrombin results in clots with an altered fiber structure: a possible mechanism of the increased thrombotic risk", Blood, vol. 101, Numer 8, pp. 3008-3013, (2003).
Wolberg, A.S., "Thrombin generation and fibrin clot structure", Blood Reviews, 21, pp. 131-142, (2007).
Wolberg, A.S., et al. "Analyzing fibrin clot structure using a microplate reader", Blood Coagulation and Fibrinolysis, vol. 13, No. 6, pp. 533-539, (2002).
Wozniak, G., "Fibrin Sealants in supporting surgical techniques: the importance of individual components", Cardiovascular Surgery, vol. 11, No. 51, pp. 17-21, (2003).
Yakoviev, S., et al., "Interaction of Fibrin(ogen) with Heparin: Further Characterization and Localization of the Heparin-Binding Site", Biochemistry, 42, pp. 7709-7716, (2003).
Young, G., et al., "Recombinant activated factor VII effectively reverses the anticoagulant effects of heparin, enoxaparin, fondaparinux, argatroban, and bivalirudin ex vivo as measured using thromboelastography", Blood Coagulation Fibrinolysis, 18, pp. 547-553, (2007).

(56) References Cited

OTHER PUBLICATIONS

Zwaai, R.F., "Membrane and lipid involvement in blood coagulation"., Biochim Biophys Acta, vol. 515, pp. 163-205, (1978).
Office Action dated May 26, 2005 for related U.S. Appl. No. 10/931,282.
Office Action dated Jul. 26, 2005 for related U.S. Appl. No. 10/931,282.
Office Action dated Jan. 31, 2006 for related U.S. Appl. No. 10/931,282.
Notice of Allowance dated Jul. 26, 2006 for related U.S. Appl. No. 10/931,282.
International Search Report and Written Opinion mailed Mar. 1, 2006, for related International Application No. PCT/US2005/029873.
Office Action dated Mar. 24, 2008 for related U.S. Appl. No. 11/362,270.
Office Action dated Sep. 17, 2008 for related U.S. Appl. No. 11/362,270.
Office Action dated Mar. 17, 2009 for related U.S. Appl. No. 11/362,270.
Office Action dated Aug. 6, 2009 for related U.S. Appl. No. 11/362,270.
International Search Report and Written Opinion mailed Oct. 5, 2006, for related International Application No. PCT/US2006/006642.
Examination Report dated Jan. 30, 2008, for related European Application No. 06 736 060.2.
Examination Report dated Dec. 19, 2008 for related European Application No. 06 736 060.2.
International Search Report mailed Dec. 22, 2006, for related International Application No. PCT/US2006/004789.
International Preliminary Report on Patentability mailed Aug. 30, 2007, for related International Application No. PCT/US2006/004789.
International Search Report and Written Opinion mailed Feb. 9, 2009, for related International Application No. PCT/US2008/082225.
International Preliminary Report of Patentability mailed Sep. 20, 2007, for related International Application No. PCT/US2006/006642.
Notice of Allowance dated Nov. 5, 2009, for U.S. Appl. No. 11/362,270.
International Search Report and Written Opinion mailed Feb. 10, 2010, for related International Application No. PCT/US2008/078584.
Examination Report dated Jun. 11, 2010 for related European Application No. 06 736 060.2.
International Preliminary Report on Patentability dated Mar. 8, 2007, for related International Application No. PCT/US2005/029873.
Examination Report dated Apr. 27, 2009 for related European Application No. 06 748 200.0.
International Preliminary Report of Patentability mailed Apr. 15, 2010, for related International Application No. PCT/US2008/078584.
International Preliminary Report of Patentability mailed May 20, 2010, for related International Application No. PCT/US2008/082225.
Invitation pursuant to Article 94(3) and Rule 71(1) EPC dated Aug. 9, 2010 for related European Application No. 06 736 060.2.

ANTICOAGULANT ANTAGONIST AND HEMOPHILIA PROCOAGULANT

CROSS REFERENCE TO RELATED APPLICATION

This application claims priority from U.S. patent application Ser. No. 12/740,762, filed Apr. 30, 2010, which is a National Stage Entry of PCT Application No. PCT/US2008/082225, filed on Nov. 3, 2008, which claims priority to U.S. Provisional Application No. 60/986,924 entitled "ANTICOAGULANT ANTAGONIST AND HEMOPHILIA PROCOAGULANT" filed 9 Nov. 2007, all of which are incorporated by reference in their entireties to the extent there is no inconsistency with the present disclosure.

FEDERALLY SPONSORED RESEARCH OR DEVELOPMENT

This application was funded in part under the following research grants and contracts: NIH (NHLBI) Grant No. R01 HL47014. The U.S. Government may have rights in this invention.

BACKGROUND

A schematic of the clotting cascades is shown in FIG. 5(A). In the figure the various clotting factors are indicated by their Roman numeral (i.e., factor VII is indicated by VII). The intrinsic pathway (also referred to as the contact pathway of blood coagulation) is initiated when contact is made between blood and certain artificial surfaces. The extrinsic pathway (also referred to as the tissue factor pathway of blood coagulation) is initiated upon vascular injury which leads to exposure of tissue factor (TF) (also identified as factor III). The dotted arrow represents a point of cross-over between the extrinsic and intrinsic pathways. The two pathways converge at the activation of factor X to Xa. Factor Xa has a role in the further activation of factor VII to VIIa. Active factor Xa hydrolyzes and activates prothrombin to thrombin. Thrombin can then activate factors XI, VIII and V furthering the cascade. Ultimately, the role of thrombin is to convert fibrinogen to fibrin, which forms clots.

Fibrinogen is the most abundant coagulation protein in blood. The formation of a fibrin clot from fibrinogen is the terminal step in the coagulation cascade. Soluble fibrin monomers, which are created when thrombin cleaves fibrinogen, spontaneously polymerize to form a three dimensional network of insoluble fibrin fibrils. Clotting of fibrinogen by thrombin is one of the few steps in the clotting cascade that does not require calcium ions. The resulting fibrin clot structure can be further stabilized via covalent cross-linking of the fibrils through the action of the transglutaminase enzyme, factor XIIIa (FIG. 5 (B)) [18].

Hemorrhage is a major complication of both naturally occurring factor deficiencies such as hemophilia, and anticoagulant therapy. Hemorrhagic episodes can result in significant patient morbidity and in rare cases, mortality. Even in patients with well-controlled stable anticoagulant therapy, emergent circumstances may arise that necessitate immediate reversal of anticoagulant status.

Rapid normalization of abnormal coagulation has generally relied on either replacement of missing factors or administration of specific antidotes [1]. A major limitation of this approach is that transfusion with human-derived products has the potential for transmission of infectious disease. Furthermore, most anticoagulant drugs, including most newly approved anticoagulant drugs, as well as some in development, lack effective antidotes [2]. In vitro studies of the effects of recombinant factor Vila (rFVIIa) [5-7] and off-label use in vivo [8-11] have indicated that rFVIIa might have a role as a general method of reversing anticoagulant therapy. Use of rFVIIa may be associated with thromboembolic adverse events [12,13]. Currently, the primary factors limiting use of rFVIIa as a universal procoagulant agent are the potential liability associated with off-label use, and the extreme expense associated with this drug.

Heparin is a naturally occurring sulfated polysaccharide. It functions as an anticoagulant by indirectly inhibiting the enzymatic activity of factor Xa and thrombin through its ability to enhance the action of the plasma anticoagulant protein, antithrombin. Heparin is widely used as a clinical anticoagulant for such indications as cardiopulmonary bypass surgery, deep vein thrombosis, pulmonary thromboembolism, arterial thrombosis, and prophylaxis against thrombosis following surgery. Therapeutic plasma concentrations of heparin are generally 0.2-0.7 units/ml. The effects of heparin can be rapidly reversed using the specific antidote protamine [1].

Low molecular weight heparins (low MW heparins), such as enoxaparin, are widely used anticoagulant drugs. Low MW heparins are size-fractionated to obtain preparations in which the heparin polymers are shorter and less heterodisperse than unfractionated heparin. Low MW heparins act primarily as factor Xa inhibitors, as they enhance antithrombin's anticoagulant effect toward factor Xa to a much greater extent than toward thrombin. Low MW heparins are widely used for longer-term anticoagulant therapy to prevent deep vein thrombosis and have certain advantages over unfractionated heparin. Therapeutic plasma concentrations of low MW heparins are generally 0.2-2 units/ml. Low MW heparins have plasma half-lives of 4-13 hours, resulting in prolonged anticoagulation even if the drug is discontinued when bleeding occurs. There is no generally accepted antidote available to reverse anticoagulation with low MW heparin.

COUMADIN® (warfarin sodium) is an oral anticoagulant drug that reduces the effective concentration of several coagulant proteins in plasma. It is widely used as long-term therapy for prevention of arterial and venous thrombosis. The most important adverse effect of COUMADIN® therapy is hemorrhage, particularly into the central nervous system. COUMADIN® therapy is typically monitored by a plasma clotting test whose readout is the International Normalized Ratio (INR). For patients receiving COUMADIN®, anticoagulant status can be immediately reversed with plasma transfusion should serious bleeding occur, but this therapy is expensive and carries risks of transfusion reactions and transmission of infectious diseases. The anticoagulant effect of COUMADIN® can be more slowly reversed with Vitamin K therapy [1].

Argatroban is an oral anticoagulant drug that is a small molecule inhibitor of thrombin. It is approved for anticoagulant therapy in patients at risk for thrombosis who cannot be treated with heparin. Therapeutic plasma concentrations are about 1 µg/ml. There is no available antidote to reverse anticoagulation with argatroban.

Rivaroxaban is an experimental anticoagulant drug under development. It functions as a small molecule inhibitor of factor Xa. It is used for prevention of thrombotic complications of orthopedic surgery. It has a plasma half-life of 7-10 hours [21]. There is no available antidote to reverse anticoagulation with rivaroxaban.

Hemophilia A is an inherited or acquired deficiency of coagulation factor VIII (FVIII) and is associated with risk of severe bleeding. Patients with hemophilia A who develop a serious bleeding episode can be treated with purified human FVIII, but this therapy is quite expensive, costing thousands of dollars per episode [3]. About one-third of patients who receive repeated doses of human FVIII will develop inhibitory antibodies to the drug, which may prevent its further use in that patient. Bleeding episodes in hemophilia patients with such inhibitory antibodies may be treated with high doses of recombinant human factor VIIa (rFVIIa); treating one bleeding episode with this drug can cost in excess of $70,000 [3,4].

Hemophilia B is an inherited or acquired deficiency of coagulation factor IX (FIX) and is associated with risk of severe bleeding. Clinical presentation and treatment are similar to that for Hemophilia A, except that injection of purified FIX is used to treat bleeding in these patients [3].

The Prothrombin Time (PT) test is widely used to monitor oral anticoagulation therapy by COUMADIN®, as a general screening test for the blood clotting system, and as the basis for specific Factor assays. Clotting times obtained with the PT are primarily dependent on the plasma levels of the vitamin K-dependent coagulation Factors II (prothrombin), VII, and X, and on the levels of two non-vitamin K-dependent proteins, Factor V and fibrinogen. The PT test is accomplished by mixing citrated plasma samples with a thromboplastin reagent and measuring the time to clot formation. The ISI value of a thromboplastin reagent is used to calculate the International Normalized Ratio (INR) for patient plasma samples; the more sensitive a thromboplastin reagent is to the changes induced by oral anticoagulant therapy, the lower its ISI value. The INR is calculated by first dividing the patient's PT value by the mean PT value for 20 or more normal plasmas. This PT ratio is then raised to the ISI power, yielding the INR value, which in turn, is used by the treating physician to adjust the drug dose. The introduction of the INR reporting system has vastly improved the standardization of monitoring of oral anticoagulant therapy, and can be credited with decreasing bleeding complications for oral anticoagulant therapy [20]. Normal plasma is defined as an INR of about 1.0. Therapeutic INR values are generally in the range of 2.0-3.5.

Polyphosphate (polyP) is a negatively charged, linear polymer of phosphate units linked by high energy phosphoanhydride bonds [14]. Dense granules of human platelets contain millimolar levels of polyP (with chain lengths of approximately 75 phosphate units) [15]. PolyP is released from platelets in response to stimulation by thrombin [17] and is cleared from plasma presumably due to degradation by plasma phosphatases [17]. We recently reported that polyphosphate is a potent hemostatic regulator, accelerating blood coagulation by activating the contact pathway of blood clotting, promoting the activation of factor V, and abrogating the function of tissue factor pathway inhibitor (TFPI) [17]. These combined effects result in a shift in the timing of thrombin generation without changing the total amount of thrombin generated. Polyphosphate also delays fibrinolysis through a thrombin-activatable fibrinolysis inhibitor (TAFI)-dependent mechanism, presumably as a consequence of an earlier burst in thrombin generation [17].

Polyphosphate, radiolabeled with $^{99m}Tc$, administered by injection, has been used as a radiopharmaceutical for skeletal imaging [16].

SUMMARY

In a first aspect, the present invention is a method for treating a coagulation deficient patient, comprising administering an amount of polyP to the patient sufficient to reduce a PT Test value or Dilute PT Test value of the plasma of the patient.

In a second aspect, the present invention is a method of reducing the effects of anticoagulant therapy on a patient, comprising administering polyP to the patient.

In a third aspect, the present invention is a method of treating hemophilia in a patient, comprising administering polyP to the patient.

In a fourth aspect, the present invention is a composition for treating a coagulation deficient patient, comprising a container, and a unit dosage of sterile polyP, in the container. The polyP is not radiolabeled.

DEFINITIONS

A coagulation deficient patient is a patient whose plasma has a PT Test value or Dilute PT Test value which is at least 1.5 times greater than that of pooled normal plasma. Pooled normal plasma is plasma prepared by mixing equal amounts of citrate-anticoagulated plasma from at least 20 normal individuals.

PolyPn means a compound of the following formula:

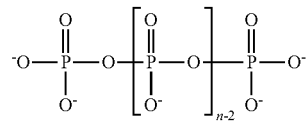

where the value of n is equal to the number of $PO_3$ units in the molecule and n is at least 3. Polyphosphate (polyP) is a generic term for $polyP_n$, including mixtures, where n of each $polyP_n$ is at least 3. Also included are salts, esters, and anhydrides of polyphosphate, as well as cyclic polyphosphates. Concentrations of polyphosphate and any $polyP_n$ may be expressed as "phosphate equivalents", which means the concentration of $PO_3$ moieties (for example, 1 μM $polyP_{75}$ is the same as 75 μM phosphate equivalents of $polyP_{75}$). All amounts and concentrations of polyP and $polyP_n$ are expressed herein as phosphate equivalents.

DETAILED DESCRIPTION

Figure 1A:
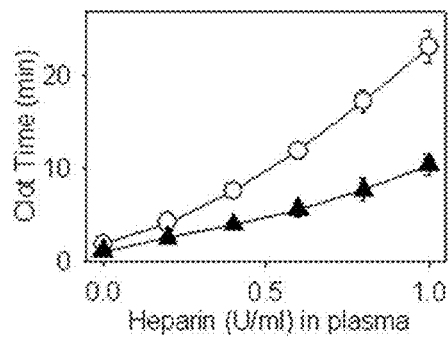
FIG. 1. PolyP antagonizes the prolongation of plasma clot time due to various anticoagulants added in vitro. Unfractionated heparin (A), enoxaparin (B), argatroban (C) and rivaroxaban (D) were added to normal human plasma at the indicated concentrations, after which clotting was initiated by a diluted thromboplastin reagent. Clot time was monitored by the Dilute PT Test. Wells without added polyP(○) were compared to those containing added 67 μM $polyP_{75}$(▲). Data are mean±se (standard error)(n=5 experiments).
Figure 1B:
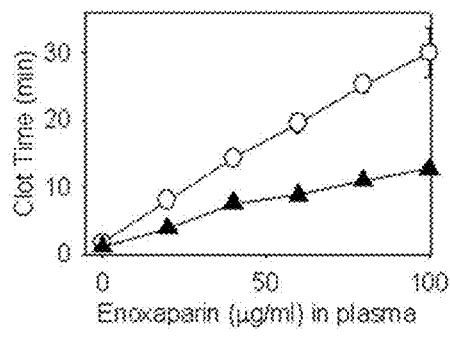
Figure 1C:
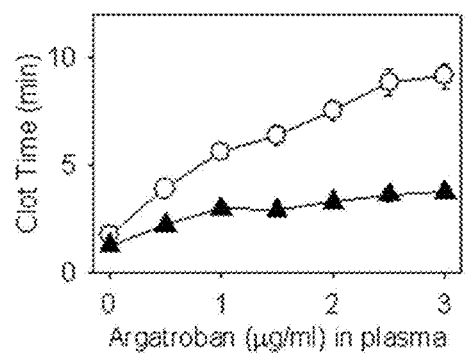
Figure 1D:
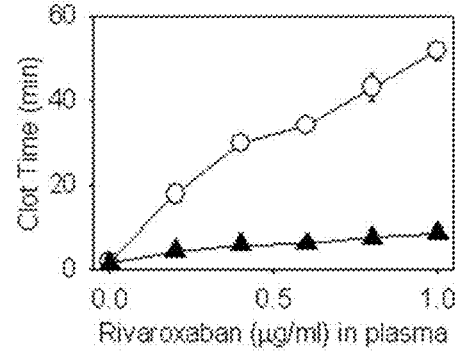
Figure 2A:
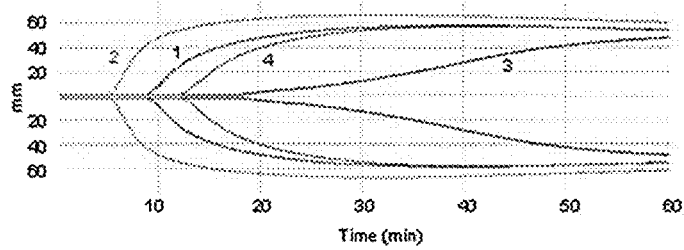
FIG. 2. Representative thromboelastography tracings for whole blood anticoagulated with various drugs added in vitro. Unfractionated heparin (A), enoxaparin (B), argatroban (C), or rivaroxaban (D) were added to fresh whole blood immediately prior to initiating coagulation with dilute thromboplastin. Each individual blood sample was divided into 4 aliquots with various additions as indicated. The 4 thromboelastography curves are for: control which consisted of blood with only buffer added (1), +100 μM polyP (2), +anticoagulant (3), and plus anticoagulant and polyP (4).
Figure 2B:
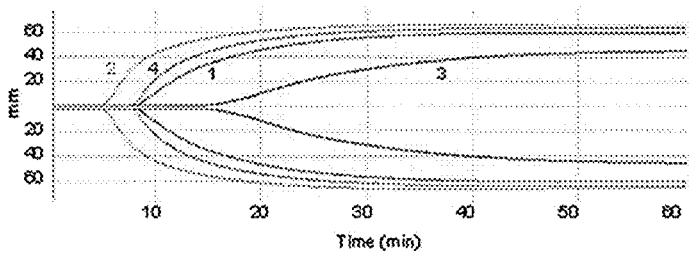
Figure 2C:
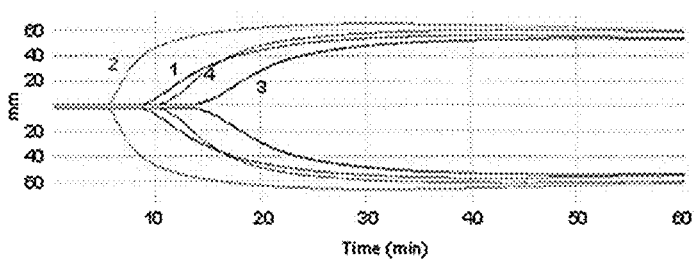
Figure 2D:
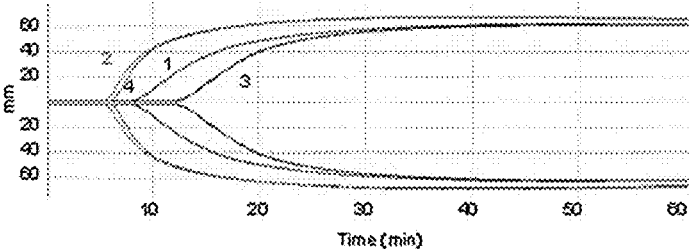

PolyP's known mechanism of action [17] is that it triggers the contact pathway of blood clotting and it accelerates the activation of factor V. In our studies with purified proteins, we found that polyP neither enhanced nor blocked the ability of antithrombin to inactivate thrombin. Furthermore, polyP did not enhance or block the ability of heparin to accelerate the inactivation of thrombin by antithrombin using purified proteins. In fact, in almost all of our studies using purified proteins, we were unable to show that polyP affected the intrinsic catalytic activity of any blood clotting enzyme we examined. The only effects of polyP that we had observed with purified proteins were the ability to trigger the activation of the contact factors, and the ability to accelerate the activation of factor V by either thrombin or factor Xa. Recently, we discovered that polyP impacts clot structure of thrombin cleaved fibrinogen, resulting in thicker fibrin fibers that are more resistant to fibrinolysis.

The present invention is based on the discovery that polyP shortens time to clot formation in plasma containing anticoagulants, and polyP normalizes clot dynamics in whole blood clotting as measured by thromboelastometry. Furthermore, polyP shortens clot time in plasma from individuals with factor deficiencies due to vitamin K antagonist therapy, and in plasma from individuals with naturally occurring hemophilia A or B. PolyP is as effective as factor replacement or rFVIIa in normalizing clot time in hemophilia plasma.

It is surprising that polyP was so effective in antagonizing the anticoagulant effect of heparins and heparinoids, and a number of small molecule drugs. The small molecule drugs target the active site of either factor Xa or thrombin, and our studies had appeared to show that polyP was without effect on the active sites of these enzymes. In the case of heparin, polyP neither enhanced nor blocked its effect when studied with purified proteins. In retrospect, we think the ability of polyP to antagonize the anticoagulant effect of these drugs is probably due to its ability to alter the timing of the burst of thrombin that occurs during blood clotting. By accelerating the conversion of factor V to Va, the blood clotting system can assemble the prothrombinase complex (the factor Va-factor Xa complex) more quickly than normal. This allows the prothrombinase complex to start functioning earlier during the life history of a blood clot than in the absence of polyP, resulting in an earlier thrombin burst. Thus, we suspect that changing the timing of assembly of the prothrombinase complex and therefore the timing of the thrombin burst is, unexpectedly, why polyP makes blood clotting much less sensitive to these anticoagulant drugs.

Administration of polyP can be used to treat a coagulation deficient patient. The treatment can be used to reduce the effects of anticoagulant therapy, and treat poisoning by anticoagulants. Examples of anticoagulants include low molecular weight heparins such as enoxaparin (LOVENOX®), dalteparin (FRAGMIN®) and tinzaparin (INNOHEP®); heparin; heparinoids such as danaparoid (ORGARAN®); pentasaccharides such as fondaparinux (ARIXTRA®); as well as argatroban, warfarin (COUMADIN®) and rivaroxaban (XARELTO®). Furthermore, administration of polyP can be used to treat hemophilia, either by chronic administration, or by acute administration to treat a bleeding episode. PolyP can also be used to treat other coagulation deficient patients, such as those suffering from liver failure and acquired hemophilia. In addition, prophylactic administration of polyP can be used prior to surgery or other activities where a coagulation deficient patient would be a risk of a bleeding episode.

Preferably, polyP is administered intravenously as a solution including a pharmaceutically acceptable carrier, such as saline. Preferably, polyP is administered as an injection, for example intravenously, intraperitoneally, subcutaneously or intramuscularly. Administration over a longer period of time may be accomplished by implanting a controlled release device, by injection of the polyP in a controlled or extended release pharmaceutically acceptable carrier, or transdermally, for example with a transdermal patch. Preferably, the polyP and solutions of polyP are sterile. Preferably, administration is by saline bolus or continuous infusion.

Preferably, administration of polyP for reversing the effects of an anticoagulant, is carried out over a period of time sufficient for the body to clear the anticoagulant. For example, low MW heparins typically have a half-life in a patient of 4-13 hours, so administration of polyP for reversing the anticoagulant effects of low MW heparins should preferably be carried out for at least 4 hours. Rivaroxaban typically has a half-life in a patient of 7-10 hours, so administration of polyP for reversing the anticoagulant effect of rivaroxaban should preferably be carried out for at least 7 hours.

The amount of polyP administered depends on the extent of coagulation deficiency, and typically is 0.1 to 100 mg per kg of body weight, such as 0.5 to 10 mg per kg of body, including 1, 2, 3, 4, 5, 6, 7, 8 and 9 mg per kg of body weight. Preferably, the total dose is diluted into 1 to 100 ml of a pharmaceutically acceptable carrier, such as saline. For extended administration, the polyP may be added to a bag of saline, such as a 1 liter bag, at a concentration sufficient to maintain the same concentration in the blood of the patient as would result from the single injection of 0.1 to 100 mg per kg of body weight. The polyP may also be provided as a unit dosage, for example as a sterile solution pre-measured in a sealed container, such as a saline solution in a syringe, with sufficient polyP for a single administration to one patient. Another example of a unit dosage would be a vial with a rubber seal containing sterile dry polyP; a syringe may be used to add saline to the vial to dissolve the polyP, which may then be drawn into the syringe for administration of the single dose. Preferably, the amount of polyP administered is sufficient to reduce the PT Test value or Dilute PT Test value of the plasma of the patient to less than 1.5, more preferably 1.4 or less, most preferably 1.2 or less, such as 1 to 1.2, times the PT Test value or Dilute PT Test value of pooled normal plasma. In the case of chronic administration, preferably the PT Test value or Dilute PT Test value of the plasma of the patient is maintained to less than 1.5, more preferably 1.4 or less, most preferably 1.2 or less, such as 1 to 1.2, times the PT Test value or Dilute PT Test value of pooled normal plasma.

The polyP contains at least 3 $PO_3$ moieties. Preferably, polyP$_n$ with n of at least 25 may be used, for example n=25-1000, more preferably, n=25-100 (including 26, 27, 28, 29, 30, 31, 32, 33, 34, 35, 36, 37, 38, 39, 40, 41, 42, 43 and 44), more preferably n is at least 45, including 45-1000 (including 70, 71, 72, 73, 74, 75, 76, 77, 78, 79 and 80).

Prothrombin Time (PT) Test clotting assays, for determining the INR value of plasma of a patient, may be performed using an ST4 coagulometer (Diagnostica Stago, Parsippany, N.J.). A 50 µL plasma sample is incubated in a cuvette for 2 min at 37° C., after which clotting is initiated by adding 100 µL pre-warmed (37° C.) thromboplastin reagent, and the time to clot formation is measured. PT Tests are typically performed in duplicate for each sample.

EXAMPLES

Anticoagulant drugs that target different aspects of the coagulation cascade were added to platelet-poor plasma and fresh whole blood in vitro. For both types of samples, clotting was initiated using a dilute thromboplastin reagent in order to approximate the nature of in vivo coagulation due to very minor trauma associated with daily activities, where clotting would be triggered by a low level of tissue factor exposure. The drugs evaluated were unfractionated heparin (an indirect inhibitor of FXa and thrombin), enoxaparin (an indirect inhibitor of FXa), argatroban (a direct inhibitor of thrombin), and rivaroxaban (a direct inhibitor of FXa). For plasma, we used concentrations of the anticoagulant drugs likely to be that associated with both therapeutic and supratherapeutic plasma levels for each individual drug (Table 1). For whole blood, pilot experiments were performed to determine a specific concentration of added drug that resulted in a prolongation of clot time by at least 1.5 to 2 fold.

TABLE 1

Concentrations of Anticoagulant

| Medication | Range added to platelet-poor plasma in vitro | Concentration added to fresh whole blood in vitro |
|---|---|---|
| Unfractionated Heparin | 0.2-1 U/mL | 0.1 U/mL |
| Enoxaparin | 20-100 µg/mL | 2.7 µg/mL |
| Argatroban | 0.5-3.0 µg/mL | 1 µg/mL |
| Rivaroxaban | 0.2-1 µg/mL | 0.2 µg/mL |

Polyphosphate antagonized the anticoagulant effect of all four drugs when added in vitro to normal plasma (FIG. 1). However, some differences were noted. For both types of heparins (unfractionated and low molecular weight), polyP shortened the clot time by approximately 50% at all concentrations of anticoagulant evaluated. Both with and without polyP, the dose-response relationship for both types of heparin was approximately linear over the concentration range tested. Consequently, addition of polyP resulted in antagonism of the anticoagulant effect of heparins by decreasing the slope of the dose-response curve, resulting in approximately 50% reversal of the effective dose. With argatroban, concentrations above 1 µg/ml failed to result in further prolongation of clot time when polyP was added. Consequently, supratherapeutic plasma levels (of 1-3 µg/ml) of argatroban were effectively reversed by polyP to result in prolongation of clot time equivalent to that obtained with argatroban levels of less than 0.5 µg/ml. PolyP was most effective at reversing the anticoagulant effect of rivaroxaban, where addition of polyP shortened the clot time by approximately 80% for all concentrations of rivaroxaban tested.

Polyphosphate also reversed the effects of each anticoagulant as measured by thromboelastography in whole blood, although the patterns of response differed somewhat between anticoagulants (FIG. 2 and Table 2) [22]. For all four anticoagulants, when polyP was added to blood containing the drug, each parameter describing clot formation was significantly changed by the addition of polyP to result in a stronger clot that formed more rapidly (denoted by superscript "b" in Table 2), indicating partial or complete reversal of the anticoagulant effect of the drug. PolyP normalized the thromboelastography parameters of the various drugs, to a different extent depending on the drug. For blood containing unfractionated heparin, polyP shortened, but did not completely normalize the time to initial increase in clot firmness (CT), whereas the parameters related to the kinetics of the increase in clot firmness (CFT and α angle) and the maximum clot firmness (MCF) were restored to values very near those of native blood. For blood containing enoxaparin, the addition of polyP normalized all parameters so that they were not different from values for native blood. For blood containing argatroban, polyP shortened but did not entirely normalize the CT. Although the difference was not statistically significant, the CFT values were shorter and the α angles steeper for blood containing polyP and argatroban than for native blood. The addition of polyP to blood containing argatroban did result in clots of significantly higher MCF than that for clots from native blood. For blood containing rivaroxaban, the addition of polyP shifted the thromboelastography curve beyond those observed for native blood, indicating complete reversal of anticoagulation.

TABLE 2

Thromboelastography Parameters

| Parameter | Control (buffer only) | +polyP | +Anticoagulant | +Anticoagulant + polyP |
|---|---|---|---|---|
| Unfractionated Heparin | | | | |
| CT (s) | 8.0 (0.4) | 5.1 (0.3)[a] | 18.8 (1.0)[a] | 11.5 (1.0)[a, b] |
| CFT (s) | 4.4 (0.7) | 1.7 (0.1)[a] | 14.9 (1.7)[a] | 4.5 (0.8)[b] |
| α angle (°) | 47.2 (4.3) | 69.6 (1.6)[a] | 18.2 (1.7)[a] | 46.8 (4.6)[b] |
| MCF (mm) | 52.8 (1.6) | 63.0 (1.8)[a] | 42.4 (2.1)[a] | 52.4 (2.7)[b] |
| Enoxaparin | | | | |
| CT (s) | 6.9 (1.8) | 4.8 (0.6)[a] | 12.9 (2.2)[a] | 8.0 (0.7)[b] |
| CFT (s) | 3.5 (0.6) | 1.6 (0.1)[a] | 7.6 (1.4)[a] | 2.7 (1.0)[b] |

TABLE 2-continued

Thromboelastography Parameters

| Parameter | Control (buffer only) | +polyP | +Anticoagulant | +Anticoagulant + polyP |
|---|---|---|---|---|
| α angle (°) | 53.0 (5.1) | 71.0 (1.2)[a] | 31.4 (5.5)[a] | 60.4 (7.8)[b] |
| MCF (mm) | 57.4 (4.9) | 64.8 (2.3)[a] | 47.0 (3.2)[a] | 59.8 (2.6)[b] |
| Argatroban | | | | |
| CT (s) | 8.1 (0.9) | 5.1 (0.6)[a] | 14.0 (1.3)[a] | 10.4 (0.9)[a, b] |
| CFT (s) | 4.4 (1.7) | 1.8 (0.5)[a] | 6.2 (2.4)[a] | 3.1 (0.5)[b] |
| α angle (°) | 48.0 (11.7) | 69.0 (6.2)[a] | 38.8 (9.4)[a] | 56.4 (3.9)[b] |
| MCF (mm) | 55.0 (7.3) | 62.2 (4.8)[a] | 49.4 (6.8)[a] | 59.4 (5.3)[a, b] |
| Rivaroxaban | | | | |
| CT (s) | 7.9 (1.8) | 5.4 (0.5)[a] | 11.7 (1.1)[a] | 6.7 (0.8)[b] |
| CFT (s) | 3.9 (0.8) | 1.7 (0.2)[a] | 4.3 (1.3) | 1.9 (0.5)[a, b] |
| α angle (°) | 49.6 (5.2) | 70.0 (2.4)[a] | 47.6 (8.5) | 67.4 (5.0)[a, b] |
| MCF (mm) | 55.4 (7.0) | 64.0 (4.5)[a] | 54.8 (8.6) | 63.6 (4.8)[a, b] |

Figure 3A:
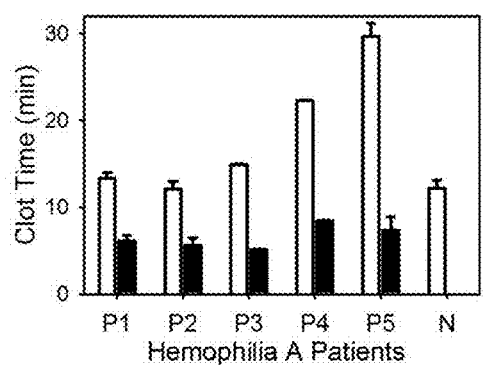
FIG. 3. PolyP shortens clot time for patients with in vivo factor deficiency by the Dilute PT Test. Clotting was initiated in plasma from 5 different patients (P1-P5, respectively) with naturally occurring hemophilia A with FVIII<1% (A), 4 different patients (P6-P9) with hemophilia B with FIX<1% (B), or plasma from 7 different patients receiving COUMADIN® with INR values as indicated (C). Clot time was monitored by the Dilute PT Test. Wells without added polyP (open bars) were compared to those containing added polyP$_{75}$ (filled bars). "N" indicates data from pooled normal plasma. Data are mean±se (n=5 repeated measurements).
Figure 3B:
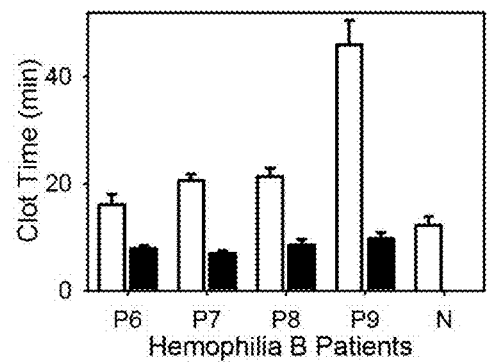
Figure 3C:
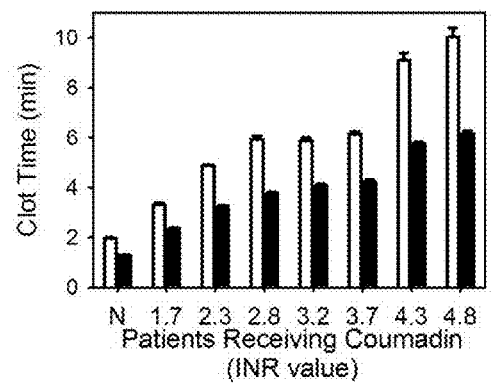
Figure 4A:
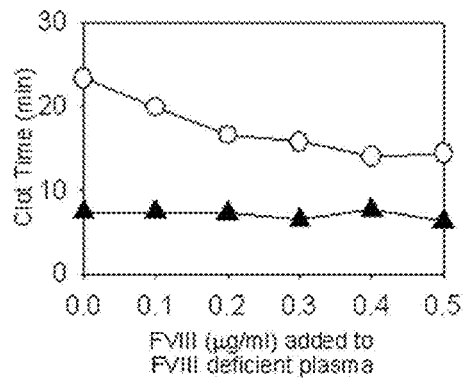
FIG. 4. PolyP shortens clot time for hemophilia patients to a greater degree than does either addition of the missing factor or rFVIIa by the Dilute PT Test. FVIII (A), or rFVIIa (B) were added to plasma from hemophilia A patient P4 and FIX (C) or rFVIIa (D) were added to plasma from hemophilia B patients P8 and P9, respectively, at the indicated concentrations. Clot time was monitored by the Dilute PT Test. Wells without added polyP(○) were compared to those containing added polyP$_{75}$ (▲). Data are mean (n=5)±se. Mean clot time for pooled normal plasma was 12.2 minutes.
Figure 4B:
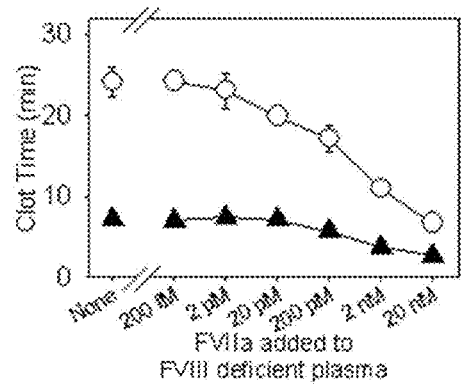
Figure 4C:
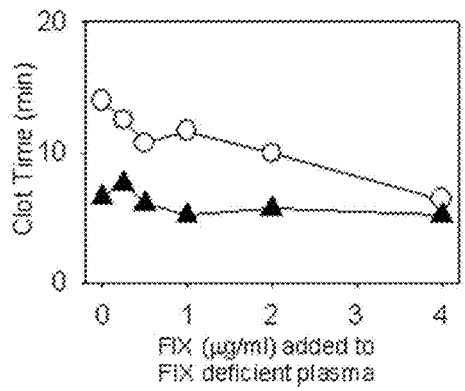
Figure 4D:
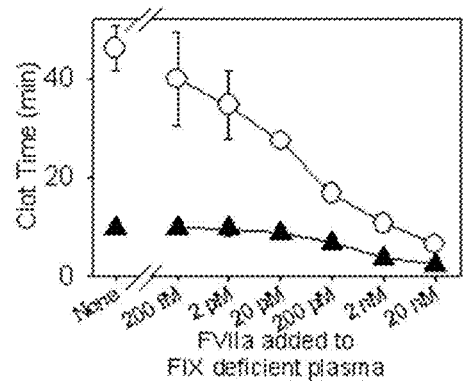
Figure 5A:
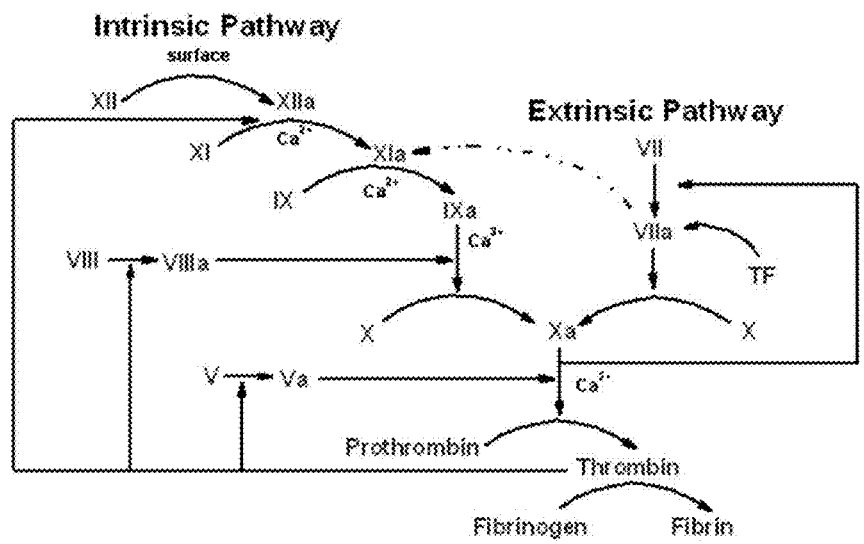
FIG. 5(A) is a schematic of the clotting cascades.
Figure 5B:
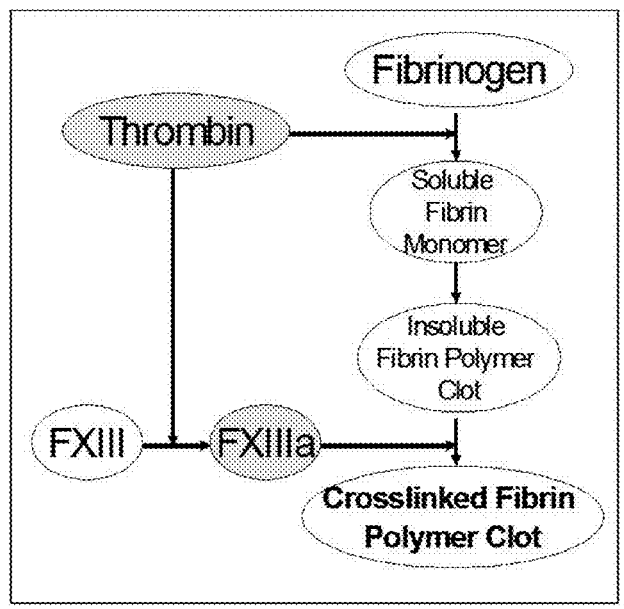
FIG. 5(B) is a schematic of the terminal steps in the blood clotting cascade.

[a] Significantly different from value for control (blood with added buffer only)
[b] Significantly different from value for blood containing anticoagulant without polyP We then proceeded to evaluate the procoagulant effects of polyP added in vitro to plasma from individuals with factor deficiencies that occurred in vivo (FIG. 3). PolyP decreased the plasma clot time for plasmas from 5 patients with severe hemophilia A and 4 patients with severe hemophilia B. In fact, in the presence of polyP, plasma from these patients clotted more rapidly than did pooled normal plasma without polyP. For patients with combined vitamin K dependent factor deficiencies (due to in vivo COUMADIN® therapy), the addition of polyP shortened, but did not completely normalize, the plasma clot time for all samples, regardless of how marked the degree of anticoagulation as measured by INR.

We further evaluated the potential effectiveness of polyP as a procoagulant for hemophilia as compared to and in conjunction with standard therapy for FVIII and FIX deficiency. Polyphosphate alone shortened the plasma clot time in both FVIII deficiency and FIX deficiency to a greater degree than did restoring the missing clotting factor to its normal plasma concentration (FIG. 4). Polyphosphate alone also shortened the plasma clot time to a degree that was similar to supplementation with 6 nM rFVIIa (for FIX-deficient plasma) or 15 nM rFVIIa (for FVIII-deficient plasma). Furthermore, the procoagulant effect of polyP was additive to that of rFVIIa at all rFVIIa concentrations evaluated.

Materials and Methods

Citrated plasma from patients with inherited FVIII deficiency (<1% activity) or FIX deficiency (<1% activity), and pooled normal plasma were from George King Biomedical (Overland Park, Kans.). Plasmas from patients stably anticoagulated with COUMADIN® were obtained from the Carle Clinic Hospital (Urbana, Ill.). Plasmas were stored frozen at −70° C., thawed at 37° C. for 5 minutes, and then held at room temperature for no more than 30 minutes prior to addition of the clotting reagent. Fresh whole blood for use in thromboelastography was collected from healthy, adult, non-smoking volunteers who were not receiving any medication. Informed consent was obtained from all volunteers for participation in the Institutional Review Board approved study.

Enoxaparin (LOVENOX®) was from Sanofi-Aventis U.S. LLC (Bridgewater, N.J.) and Argatroban was from GlaxoSmithKline (Research Triangle Park, N.C.). Rivaroxaban (XARELTO®) was from Bayer HealthCare (Berkeley, Calif.). Unfractionated heparin and polyP$_{75}$, a polyP preparation containing a mean polymer size of approximately 75, were from Sigma Aldrich (St. Louis, Mo.). Concentrations of polyP are expressed in terms of phosphate monomer. Recombinant human factor VIIa (FVIIa) was purchased from American Diagnostica (Stamford, Conn.), recombinant human factor VIII (FVIII, KOGENATE-FS®) was from Bayer HealthCare (Berkeley, Calif.), and human factor IX (FIX) was purchased from Enzyme Research Laboratories (South Bend, Ind.). Relipidated recombinant tissue factor (HEMOLIANCE® RecombiPlasTin) was from Instrumentation Laboratory (Lexington, Mass.) and dried recombinant human tissue factor with calcium (DADE® INNOVIN®) was from Dade Behring (Newark, Del.).

Evaluation of Clot Formation in Plasma Samples with the Dilute PT Test

The following describes the use of the Dilute PT Test to evaluate the effectiveness of polyP in treat hemophilia and reversing the effects of anticoagulant drugs. Anticoagulant drugs were added to pooled normal plasma in vitro at concentrations of up 1 U/mL for unfractionated heparin, 100 µg/mL for enoxaparin, 3 µg/mL for argatroban, and 1 µg/mL for rivaroxaban. Plasma from a patient deficient in FVIII was evaluated with and without the addition of up to 0.5 µg/mL FVIII or 20 nM FVIIa. Plasma from a patient deficient in FIX was evaluated with and without the addition of up to 4 µg/mL FIX or 20 nM FVIIa. INR values for samples from patients receiving COUMADIN® ranged from 1.7 to 4.8.

Plasma clots were formed in 96-well medium binding polystyrene microplates (Corning Inc., Corning, N.Y.). Plasma (80 µL) was added to the well and clotting was initiated by addition of 160 uL of clotting reagent. The clotting reagent consisted of RecombiPlasTin (as a source of tissue factor) diluted 200 fold (for normal and anticoagulated plasmas) or 8000 fold (for hemophilia plasmas) into buffer containing 100 µM phospholipid vesicles (20% phosphatidylserine and 80% phosphatidylcholine made by sonication), 12.5 mM CaCl$_2$, 25 mM Tris HCl pH 7.4, 0.1% bovine serum albumin, and 150 mM NaCl. Clotting reagent was divided into reagent without added polyP and reagent with added 100 µM polyP$_{75}$.

Clotting was evaluated by monitoring the change in turbidity (A$_{405}$) for 1 hour at room temperature using Softmax software and a Spectramax microplate reader (Molecular Devices Corporation, Sunnyvale, Calif.). Clotting time was calculated from these data using SigmaPlot version 7.101 (SPSS, Inc) to fit a line to the steepest segment of the absorbance curve and then determining the intersection of this line with the initial baseline A$_{405}$ (representing the lag phase prior to clot formation). All assays were repeated 5 times.

Whole Blood Thromboelastometry

Thromboelastography was carried out using the ROTEM® four channel system (Pentapharm, Munich, Germany) using the supplied software package. Fresh, non-anticoagulated whole blood was collected via atraumatic venipuncture using a two-syringe technique. The initial 3 ml of blood was discarded and the blood sample to be used was then drawn into a 3 ml plain plastic syringe. The blood was immediately transferred to the supplied disposable plastic cups (280 μL per cup) and thoroughly mixed with 20 μL buffer (TBS: 50 mM Tris-HCl pH 7.4, 150 mM NaCl, 0.02% $NaN_3$) or additives in TBS. Each fresh whole blood sample was divided into 4 cups containing the following: TBS only (control), $polyP_{75}$, anticoagulant drug only, or both $polyP_{75}$ and anticoagulant drug. Clotting was then initiated immediately via addition of 20 μL of tissue factor containing clotting reagent (INNOVIN® diluted in TBS). Thromboelastography measurement was initiated within 120 seconds of blood drawing for all samples. The final concentrations in the reaction were 87.5% whole blood, INNOVIN® diluted 1:17,000, 0 or 100 μM polyP, 0 or added anticoagulant drug (0.1 U/mL unfractionated heparin or 2.7 μg/mL enoxaparin or 1 μg/mL argatroban, or 0.2 μg/mL rivaroxaban). The measurements were continued for 2 hours and the clot time (CT), clot formation time (CFT), alpha angle (α angle), and maximum clot firmness (MCF) were recorded as supplied by the ROTEM® software. Each anticoagulant drug was added in vitro to whole blood from 5 different individuals.

Statistical Analysis

Statistical analyses were performed using SigmaStat statistical software version 2.03 (SPSS, Inc). In all cases, two-tailed t-tests were conducted at the 0.05 level of significance. Clot times obtained using the Dilute PT Test with and without added polyP in plasma-based experiments were compared using unpaired t-tests. Results for each variable obtained from the ROTEM® experiments (CT, CFT, a angle, MCF) were compared separately. For each group of anticoagulants, parameters obtained for control blood samples were compared to those for blood+polyP, blood+anticoagulant, and blood+anticoagulant+polyP. The latter two samples were also directly compared. To account for inter-individual variation, thromboelstography parameters were compared using paired t-tests.

REFERENCES

1. Schulman S, Bijsterveld N R. Anticoagulants and their reversal. Transfus. Med. Rev. 2007; 21:37-48.
2. Kessler C M. Current and future challenges of antithrombotic agents and anticoagulants: Strategies for reversal of hemorrhagic complications. Semin. Hematol. 2004; 41:44-50.
3. Mathew P. Current opinion on inhibitor treatment options. Semin. Hematol. 2006; 43:58-13.
4. Hoots W K. Challenges in the therapeutic use of a "so-called" universal hemostatic agent: recombinant factor VIIa. Hematology Am. Soc. Hematol. Educ. Program. 2006; 426-431.
5. Young G, Yonekawa K E, Nakagawa P A et al. Recombinant activated factor VII effectively reverses the anticoagulant effects of heparin, enoxaparin, fondaparinux, argatroban, and bivalirudin ex vivo as measured using thromboelastography. Blood Coagul. Fibrinolysis 2007; 18:547-553.
6. Gerotziafas G T, Depasse F, Chakroun T, Samama M M, Elalamy I. Recombinant factor VIIa partially reverses the inhibitory effect of fondaparinux on thrombin generation after tissue factor activation in platelet rich plasma and whole blood. Thromb. Haemost. 2004; 91:531-537.
7. Lisman T, Bijsterveld N R, Adelmeijer J et al. Recombinant factor VIIa reverses the in vitro and ex vivo anticoagulant and profibrinolytic effects of fondaparinux. J. Thromb. Haemost. 2003; 1:2368-2373.
8. Firozvi K, Deveras R A, Kessler C M. Reversal of low-molecular-weight heparin-induced bleeding in patients with pre-existing hypercoagulable states with human recombinant activated factor VII concentrate. Am. J. Hematol. 2006; 81:582-589.
9. Oh J J, Akers W S, Lewis D, Ramaiah C, Flynn J D. Recombinant factor VIIa for refractory bleeding after cardiac surgery secondary to anticoagulation with the direct thrombin inhibitor lepirudin. Pharmacotherapy 2006; 26:569-577.
10. Brody D L, Aiyagari V, Shackleford A M, Diringer M N. Use of recombinant factor VIIa in patients with warfarin-associated intracranial hemorrhage. Neurocrit. Care 2005; 2:263-267.
11. Lin J, Hanigan W C, Tarantino M, Wang J. The use of recombinant activated factor VII to reverse warfarin-induced anticoagulation in patients with hemorrhages in the central nervous system: preliminary findings. J. Neurosurg. 2003; 98:737-740.
12. O'Connell K A, Wood J J, Wise R P, Lozier J N, Braun M M. Thromboembolic adverse events after use of recombinant human coagulation factor VIIa. JAMA 2006; 295:293-298.
13. Aledort L M. Comparative thrombotic event incidence after infusion of recombinant factor VIIa versus factor VIII inhibitor bypass activity. J. Thromb. Haemost. 2004; 2:1700-1708.
14. Kornberg A, Rao N N, ult-Riche D. Inorganic polyphosphate: a molecule of many functions. Annu. Rev. Biochem. 1999; 68:89-125.
15. Ruiz F A, Lea C R, Oldfield E, Docampo R. Human platelet dense granules contain polyphosphate and are similar to acidocalcisomes of bacteria and unicellular eukaryotes. J. Biol. Chem. 2004; 279:44250-44257.
16. Krishnamurthy G T, Tubis M, Endow J S, Singhi V, Walsh C F, Bland W H. Clinical comparison of the kinetics of $^{99m}$Tc-labeled polyphosphate and diphosphonate. J Nuc Med. 1974; 15(10):848-855.
17. Smith S A, Mutch N J, Baskar D et al. Polyphosphate modulates blood coagulation and fibrinolysis. Proc. Natl. Acad. Sci. U.S.A 2006; 103:903-908.
18. Mosseson M W, Fibrinogen and fibrin structure and functions. J Thromb Haemost 3: 1894-1904, 2005.
19. Morrissey J H, et al. COAGULATION AND FIBRINOLYTIC CASCADES MODULATOR, U.S. Patent Application Publication, Pub. No. US 2006/0198837 A1, Sep. 7, 2006.
20. Hirsh J, Fuster V, Ansell J, Halperin J L. American Heart Association/American College of Cardiology Foundation guide to warfarin therapy. *Circulation* 2003; 107:1692-1711.
21. Kubitza D, Becka M, Wensing, G, Voith B, Zuehlsdorf M. Safety, pharmacodynamics, and pharmacokinetics BAY 59-7939—an oral, direct Factor Xa inhibitor-after multiple dosing in healthy male subjects. Eur J Clin Pharmacol 2005; 61:873-880.
22. Luddington, R J. Thromboelastography/Thromboelastometry. Clin Lab Hemost 2006; 27:81-90.

What is claimed is:

1. A method of reducing the effects of an anticoagulant drug on a patient, comprising administering an amount of a polyphosphate (polyP) to a patient who has been administered the anticoagulant drug, wherein the polyP is polyP$_n$ and n is at least 25, and wherein the polyP reduces the clotting time of plasma or whole blood of the patient containing the anticoagulant drug.

2. The method of claim 1, wherein the anticoagulant drug is a direct thrombin inhibitor, a direct factor Xa inhibitor, a vitamin K antagonist, heparin, or a heparinoid.

3. The method of claim 1, wherein the anticoagulant drug is selected from the group consisting of heparin, warfarin, argatroban, rivaroxaban, heparinoids, low molecular weight heparins and combinations thereof.

4. The method of claim 1, wherein the amount of polyP administered to the patient is between 0.1 to 100 mg per kg of body weight of the patient.

5. The method of claim 1, wherein a Prothrombin Time (PT) Test value or a Dilute PT Test value on plasma from the patient is increased by at least 1.5 times compared to normal pooled plasma due to the administration of the anticoagulant drug, and wherein the amount of polyP administered to the patient is sufficient to reduce the PT Test value or Dilute PT Test value of plasma of the patient to less than 1.5 times greater than the PT Test value or Dilute PT Test value of pooled normal plasma.

6. The method of claim 1, wherein the amount of polyP administered to the patient is between 0.5 to 10 mg per kg of body weight of the patient, the polyP is administered intravenously, and the PT Test value or Dilute PT Test value of the plasma of the patient is reduced to less than 1.2 times greater than the PT Test value or Dilute PT Test value of pooled normal plasma.

7. The method of claim 1, wherein the amount of polyP administered to the patient is sufficient so that plasma of the patient treated with the polyP clots more rapidly than pooled normal plasma.

8. The method of claim 1, wherein the polyP is polyP$_n$, and n is 25-1000.

9. The method of claim 1, wherein the polyP is polyP$_n$, and n is 25-100.

10. The method of claim 1, wherein the polyP is administered by injection.

11. The method of claim 1, wherein the polyP is administered intravenously.

12. The method of claim 1, wherein the polyP is administered over a period of time sufficient for the body of the patient to clear the anticoagulant drug.

* * * * *